United States Patent [19]

Aaronson et al.

[11] Patent Number: 4,822,916

[45] Date of Patent: Apr. 18, 1989

[54] PREPARATION OF DIARYL SULFONES

[75] Inventors: Alan M. Aaronson, Flushing Meadows; Robert L. Protzmann, New City; John Tomko, Dobbs Ferry, all of N.Y.

[73] Assignee: Akzo America Inc., New York, N.Y.

[21] Appl. No.: 99,265

[22] Filed: Sep. 21, 1987

[51] Int. Cl.[4] .......................................... C07C 147/06
[52] U.S. Cl. ...................................................... 568/34
[58] Field of Search ...................... 568/28, 29, 30, 31, 568/32, 33, 34

[56] References Cited

U.S. PATENT DOCUMENTS

| | | | |
|---|---|---|---|
| 3,125,604 | 3/1964 | Robbins | 568/34 |
| 3,501,532 | 3/1970 | Minor et al. | 568/34 |
| 3,579,590 | 5/1971 | Davis | 568/34 |
| 3,673,259 | 6/1972 | Rosin et al. | 568/34 |
| 3,729,517 | 4/1973 | Bracke | 568/34 |
| 3,855,312 | 12/1974 | Horner | 568/34 |
| 4,554,381 | 11/1985 | Desbois | 568/34 |
| 4,558,161 | 12/1985 | Morita et al. | 568/34 |

FOREIGN PATENT DOCUMENTS 8206551  1/1983  Japan .................................... 568/34

OTHER PUBLICATIONS

T. Kurano et al., Chemical Abstracts, vol. 70, No. 57419t (1969), Diaryl Sulfones.

*Primary Examiner*—Mary E. Ceperley
*Attorney, Agent, or Firm*—Richard P. Fennelly; Louis A. Morris

[57] ABSTRACT

Diaryl sulfones are formed in a two-stage procedure. The first involves the reaction of an aryl sulfonic acid with an aryl reagent containing active hydrogen while by-product water is removed azeotropically. In the second stage, which contains unreacted sulfonic acid, is treated with a sulfone condensing agent and additional aryl reagent to react additional, unreacted aryl sulfonic acid from the first stage.

6 Claims, No Drawings

PREPARATION OF DIARYL SULFONES

BACKGROUND OF THE PRESENT INVENTION

1. Field of the Invention

Diaryl sulfones are useful as polymer additives and as intermediates for the preparation of polymers. The present invention is a process for their production by reacting an aryl sulfonic acid with an aryl reagent containing an active hydrogen atom.

2. Description of the Prior Art

A number of processes have been described in the literature for the manufacture of diaryl sulfones, including the following:

U.S. Pat. No. 3,125,604 to G. B. Robbins teaches reaction of an aryl sulfonic acid and a nonsulfonated hydrogen-aryl compound in the presence of a pentavalent phosphorus halide which acts as a condensing agent for the reaction.

U.S. Pat. No. 3,501,532 to J. T. Minor et al. teaches the reaction of an aromatic sulfonic acid with an aromatic compound having a replaceable hydrogen atom in the presence of a polyphosphoric acid having a phosphoric anhydride content of from about 75-85% which acts as a condensing agent.

U.S. Pat. No. 3,579,590 to D. S. Davis teaches production of diaryl sulfones by reacting aryl compounds having an active hydrogen, anhydrous sulfonating agent, and a non-metallic condensing agent (e.g., $P_2O_5$, phosphorus pentachloride, phosphorus oxychloride, and boric anhydride).

U.S. Pat. No. 3,673,259 to J. Rosin et al. advocates the condensation reaction of an arylsulfonyl chloride with an arene by conducting the condensation reaction in the presence of relatively large amounts of a particular arylsulfonic acid which corresponds to such arylsulfonic chloride, substantially in the absence of any metal salts.

U.S. Pat. No. 3,729,517 to W. J. I. Bracke teaches formation of dialkaryl sulfones by first treating an alkaryl compound with concentrated sulfuric acid in a first step to convert it to a sulfonic acid with the second stage being initiated by a catalytic amount of $P_2O_5$ to merely initiate the reaction with water thereafter being distilled off azeotropically.

U.S. Pat. No. 3,855,312 to P. J. Horner relates to a process for preparation of di-4-chlorophenyl sulphone in which a reaction mixture containing 4-chlorobenzenesulphonic acid and chlorobenzene is reacted at elevated temperature and superatmospheric pressure, water is removed as it is formed, and water and accompanying chlorobenzene are condensed and separated with the chlorobenzene being returned to the reaction mixture.

U.S. Pat. No. 4,558,161 to Y. Morita et al. covers reaction of chlorosulfonic acid with a mixture of an aromatic hydrocarbon and an aromatic sulfonic acid with hydrochloric acid gas evolved during the reaction being continuously removed.

Chemical Abstracts, Vol. 70, 57419t (1969), abstracting Japanese No. 68 24,662, describes reaction of an aromatic sulfonic acid with an aromatic hydrocarbon in the presence of a phosphorus oxide dehydrating agent, such as $P_2O_5$.

SUMMARY OF THE PRESENT INVENTION

The instant invention is a process for forming diaryl sulfones by first reacting an aryl sulfonic acid with an aryl reagent containing active hydrogen while removing water by-product therefrom to aid in their conversion to the desired diaryl sulfone. The reaction product from this step, which contains unreacted aryl sulfonic acid and diaryl sulfone product, is thereafter reacted with further aryl reagent and with a sulfone condensing agent to increase the amount of aryl sulfonic acid converted to the desired diaryl sulfone.

DETAILED DESCRIPTION OF THE PRESENT INVENTION

The diaryl sulfones intended to be produced by the instant process have the formula Ar—$SO_2$—Ar, with Ar representing a substituted or unsubstituted aryl radical such as phenyl, halophenyl (e.g., para-chlorophenyl), and the like. The aryl reagent containing active hydrogen can have the formula H—Ar with Ar being as defined above. The sulfonic acid moiety can be Ar—$SO_3H$. In any of the foregoing formulae, Ar can be the same or different so that the process is amenable to the formation of diaryl sulfones having either the same or differing Ar groups.

The first stage reaction between sulfonic acid and aryl reagent is conducted at temperatures of from about 80° C. to about 250° C. using molar ratios of sulfonic acid to aryl reagent of about 1:1 to about 1:10 at either atmospheric or positive pressure (up to about 100 psi) while by-product water is removed by azeotroping. The reaction mixture thus produced will contain the desired diaryl sulfone (in about 60 to 70% by yield, based on the amount of starting sulfonic acid).

The reaction mixture resulting from the aforementioned process is then combined with an effective, preferably stoichiometric, amount (e.g., 100% or more based on the amount of unreacted sulfonic acid) of a sulfone condensing agent and additional aryl reagent so that additional sulfonic acid can be reacted and converted to the diaryl sulfone. Preferably, from about 100% to about 200% or more of condensing agent, based on the weight of unreacted sulfonic acid will be useful. Representative condensing agents include the pentavalent phosphorus halides ($PCl_5$, $PBr_5$, $POCl_3$ or $POBr_3$), $P_2O_5$, boric anhydride, and the like. The treatment in this stage of the reaction increases the yield of diaryl sulfone based on the amount of sulfonic acid, from 60%–70% after the first stage to the neighborhood of 95%–100%, if desired.

The use of the sulfone condensing agent to aid in driving the reaction towards completion only after it has initially been run has certain advantages over the inclusion of the condensing agent from the start of the reaction. Firstly, when the condensing agent is expensive (e.g., $P_2O_5$) less will be used since only a portion of the sulfonic acid used in the overall process will be present when the condensing agent is present. Secondly, in those cases in which the condensing agent gives rise to solids formation in the reaction medium, causing stirring problems and the like, the use of a lessened overall amount of condensing agent in only a portion of the reaction will tend to ameliorate any such problems that might occur. Thirdly, deactivation of the condensing agent (e.g., $P_2O_5$) by reaction by-products (e.g., polyphosphoric acid) formed during the sulfonic acid/aryl reagent reaction will also be lessened if the condensing agent is present during only the latter portions of the overall reaction after some substantial conversion to the desired sulfone end product has already taken place.

In accordance with the present invention, an essentially complete reaction is achieved at moderate reaction temperature and at atmospheric pressure. It has been found, in regard to use of $P_2O_5$ as a sulfone condensing agent, that there is a substantial reduction of the color of the reaction mixture so as to afford a one-step crystallization of good purity product without the need for use of decolorizing agents, such as activated carbon.

The following examples illustrate certain embodiments of the present invention.

EXAMPLE 1

Parachlorobenzenesulfonic acid (150 gm, 0.78 mole) was placed in a 500 cc, three-neck flask fitted with a magnetic stirrer, heating mantle, reflux condenser, dropping funnel and a reverse Dean Stark trap. The acid was then heated and stirred as monochlorobenzene (MCB) was added dropwise at a rate permitting sufficient azeotroping of water without excessive cooling of the reaction mixture. The following results illustrate the reaction:

| Time (hrs/min) | Pot Temp. (°C.) | Vapor Temp. (H°C.) | Total MCB added (cc) | $H_2O$ Collected (cc) |
|---|---|---|---|---|
| 0/0 | 25 | 25 | 20 | — |
| 1/00 | 190 | 131 | 20 | 1.0 |
| 1/45 | 250 | 131 | 20 | 2.0 |
| 2/00 | 250 | 131 | — | 4.0 |
| 3/00 | 250 | 131 | 45 | 9.0 |
| 5/00 | 250 | 131 | 55 | 10.0 |

The conversion to the sulfone of para-chlorobenzene was 28% as measured by high pressure liquid chromatography.

EXAMPLE 2

Into a 500 cc flask, fitted with a mechanical stirrer, solid addition funnel, thermometer, and heating mantle was placed about 90% of the product of Example 1 and a 400% molar excess of monochlorobenzene. The mixture was heated, stirred and $P_2O_5$ was added in small portions from the addition funnel as follows:

| Time (hr/min) | Pot Temp. (°C.) | Total $P_2O_5$ Added (gm) |
|---|---|---|
| 0/0 | 100 | 0 |
| 0/35 | 130 | 15 |
| 1/45 | 132 | 50 |
| 3/00 | 133 | 75 |
| 5/45 | 133 | 86.5 |

The conversion of the unreacted parachlorobenzenesulfonic acid contained in the product from Example 1 to the desired sulfone was essentially 100% as measured by high pressure liquid chromatography.

The foregoing examples are presented to illustrate certain embodiments of the present invention and should, therefore, not be construed in a limiting sense. The scope of protection which is sought is set forth in the claims which follow.

We claim:

1. A process for forming diaryl sulfones which comprises:
   (a) reacting an aryl sulfonic acid with an aryl reagent containing active hydrogen while removing water by-product therefrom to aid in the conversion to the diaryl sulfone so as to achieve a yield of diaryl sulfone that is no less than about 60%, based on the amount of aryl sulfonic acid; and
   (b) thereafter reacting the product from step (a), which comprises unreacted aryl sulfonic acid and diaryl sulfone product, with further aryl reagent containing active hydrogen and an added effective amount of sulfone condensing agent, said amount aiding in driving the process towards completion only after it has been initially run as defined in (a), to increase the amount of aryl sulfonic acid converted to diaryl sulfone by the reaction of the unreacted aryl sulfonic acid and aryl reagent containing active hydrogen.

2. A process as claimed in claim 1 wherein the sulfone condensing agent is $P_2O_5$.

3. A process as claimed in claim 1 wherein the sulfone condensing agent is present in at least about 100% by weight, based on the amount of unreacted aryl sulfonic acid.

4. A process as claimed in claim 2 wherein the sulfone condensing agent is present in at least about 100% by weight, based on the amount of unreacted aryl sulfonic acid.

5. A process as claimed in claim 1 wherein the aryl sulfonic acid is a chlorobenzenesulfonic acid and the aryl reagent is a chlorobenzene.

6. A process as claimed in claim 4 wherein the aryl sulfonic acid is a chlorobenzenesulfonic acid and the aryl reagent is a chlorobenzene.

* * * * *